United States Patent [19]

Kenichiro et al.

[11] Patent Number: 4,749,650
[45] Date of Patent: Jun. 7, 1988

[54] BACILLUS CONTAINING A 5'INOSINATE DEHYDROCENASE GENE

[75] Inventors: Miyagawa Kenichiro, Ibaraki; Nakahama Kazuo, Nagaokakyo; Kikuchi Masakazu, Toyono; Doi Muneharu, Takarazuka, all of Japan

[73] Assignee: Takeda Chemical Industries, Ltd., Osaka, Japan

[21] Appl. No.: 671,482

[22] Filed: Nov. 14, 1984

[30] Foreign Application Priority Data

Jan. 27, 1984 [JP] Japan .................. 59-13968

[51] Int. Cl.$^4$ .................. C12P 19/40; C12N 1/20; C12N 1/100; C07H 21/04
[52] U.S. Cl. .................. 435/88; 435/253; 435/320; 536/27
[58] Field of Search .................. 536/27; 435/172.3, 88, 435/190, 253, 317

[56] References Cited

FOREIGN PATENT DOCUMENTS 58-175493 4/1982 Japan .

OTHER PUBLICATIONS

*Biochemistry,* Lehninger, pp. 729-735, (2d ed.).
Matsui et al, *Agric. Biol. Chem.,* 43, 1739-1744 (1979).
Miyagawa et al, *Biotechnology,* 4, pp. 225-228 (1986).

*Primary Examiner*—Blondel Hazel
*Assistant Examiner*—Veronica Dutch
*Attorney, Agent, or Firm*—David G. Conlin; Stephan P. Williams

[57] ABSTRACT

A DNA having a 5'-inosinate dehydrogenase gene and further having a Hind III cleavage site 2.9 kilo base pairs can be produced from the chromosomal DNA of a guanosine and/or xanthosine-producing strain of the genus Bacillus. A vector with the DNA obtained above is used to transform Bacillus strain capable of producing guanosine, and the transformed Bacillus strain is useful to increase the guanosine productivity as compared with the case in which a strain before transformantion is used.

6 Claims, 2 Drawing Sheets

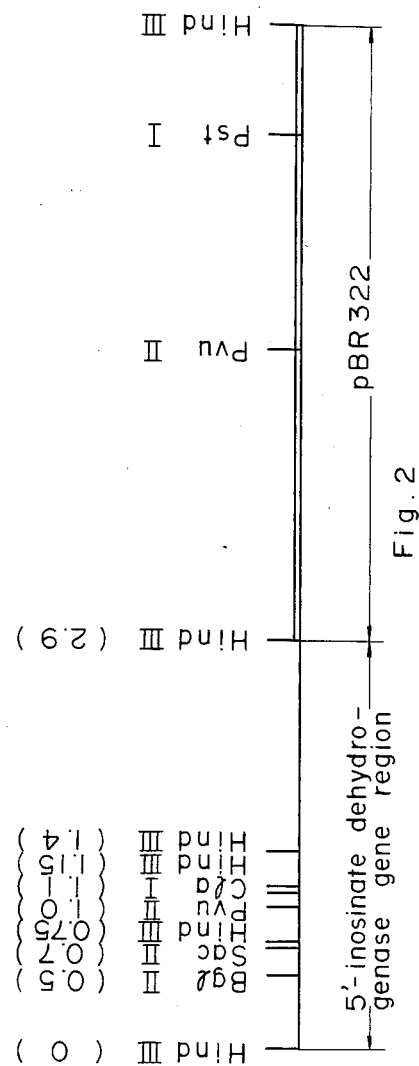
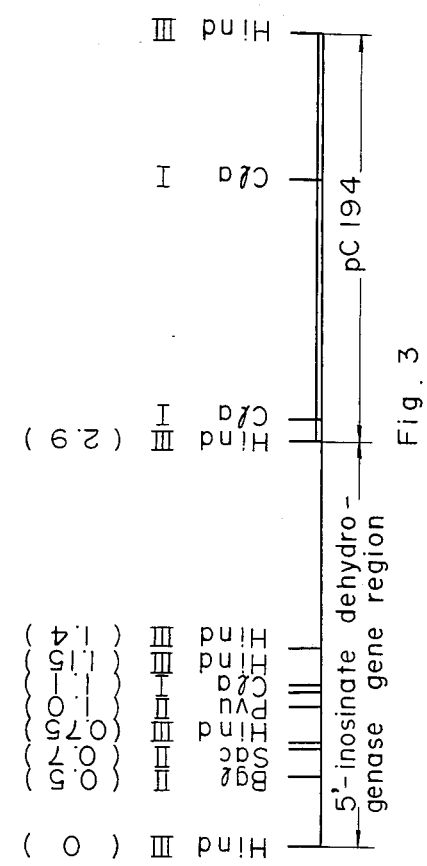

BACILLUS CONTAINING A 5'INOSINATE DEHYDROCENASE GENE

This invention relates to a DNA having a 5'-inosinate dehydrogenase gene, a vector with the same DNA inserted therein, a Bacillus strain transformed with said vector, and a method of producing guanosine which comprises cultivating the transformant.

Guanosine is a substance of importance as a starting material in the synthesis of 5'-guanylic acid which is a seasoning chemical, and its large-scale production at a low cost is of great significance from the industrial viewpoint. Heretofore, mutants which are adenine-requiring mutants possessing particular properties such as nucleotide phosphorylase deficiency, GMP reductase deficiency and adenine-adenosine resistance, among others, have been used in producing guanosine by fermentative processes.

In accordance with the present invention, it has been found that transformation of an inosine- and/or guanosine-producing strain of the genus Bacillus with a vector DNA with a 5'-inosinate dehydrogenase gene region derived from a guanosine- and/or xanthosine-producing microorganism as inserted therein can result in a marked increase in the accumulation of guanosine.

Thus, the invention is concerned with (1) a DNA having a 5'-inosinate dehydrogenase gene and further having a Hind III cleavage site 2.9 kilo base pairs apart therefrom; (2) the DNA mentioned above under (1) as obtained from the chromosomal DNA of a guanosine and/or xanthosine-producing strain of the genus Bacillus; (3) a vector with the DNA mentioned above under (2) inserted therein; (4) a Bacillus strain transformed with the vector mentioned above under (3); (5) the Bacillus strain mentioned above under (4) as transformed with the vector mentioned above under (3), said strain being capable of producing guanosine; and (6) a method of producing guanosine which comprises cultivating in a medium a guanosine-producing Bacillus strain transformed with a vector with a 5'-inosinate dehydrogenase gene region obtained from the chromosomal DNA of a guanosine- and/or xanthosine-producing Bacillus strain as inserted wherein and recovering the guanosine thereby produced and accumulated in the culture.

The DNA according to the invention is obtained from a microorganism having a 5'-inosinate dehydrogenase gene. As this donor microorganism, there is generally used a guanosine- and/or xanthosine-producing microorganism. Even a microorganism incapable of producing either substance can be used as the DNA donor in the practice of the present invention, if the 5'-inosinate dehydrogenase of said microorganism is wholly or partly free from the feedback control by purine substances. Thus, for instance, guanosine- and/or xanthosine-producing Bacillus strains are examples of the donor microorganism, and their chromosomal DNA can serve as an isolation source. Exemplary donor microorganisms are *Bacillus subtilis*, *Bacillus pumilus* or *Bacillus licheniformis* strains. More specifically, such Bacillus strains are *Bacillus subtilis* NA-6011 (IFO 14189, FERM BP-291), *Bacillus substilis* NA-6012 (IFO 14190, FERM BP-292), *Bacillus subtilis* NA-7821 (IFO 14368, FERM BP-618), *Bacillus subtilis* ATCC 19221, *Bacillus pumilus* NA-1102 (IFO 14185, FERM BP-289), *Bacillus pumilus* NA-1103 (IFO 14186, FERM BP-290).

The chromosomal DNA is prepared from the donor microorganism by conventional methods, for example by extracting the chromosomal DNA with phenol.

The chromosomal DNA obtained from the donor is cleaved with restriction enzymes to thereby prepare a DNA fragment which has a 5'-inosinate dehydrogenase gene and further has a Hind III cleavage site 2.9 kilo base pairs apart therefrom. In preparing such DNA fragment, appropriate restriction enzymes can be selected from among restriction enzymes described in a variety of documents (e.g. Takara Reagents for Genetic Engineering Research, published by Takara Shuzo Co. Ltd. Japan). Specific examples of such restriction enzyme include Pst I, Pvu I or Hind III and so on.

The thus-obtained, 5'-inosinate dehydrogenase gene region-containing chromosomal DNA fragment is then inserted into a vector DNA. Suitable DNA vectors include pUB110 [J. Bacteriol., 134, 318 (1978)], pT127, pC194, pC221[Proc. Natl. Acad. Sci. U.S.A., 74, 1680 (1977)] and pLS28 [J. Bacteriol., 131, 699 (1977)], or any newly isolated or synthesized ones provided that it is usable as a vector DNA in Bacillus strains. The vector DNA is cleaved with the same restriction enzymes as used in the above-mentioned chromosomal DNA fragment preparation.

The thus-obtained, 5'-inosinate dehydrogenase gene region-containing chromosomal DNA fragment, is ligated with the cleaved vector DNA by the conventional DNA ligase method [Proc. Natl. Acad. Sci. U.S.A., 57, 1426 (1967)], the terminal transferase method [Proc. Natl. Acad. Sci. U.S.A., 69, 2904 (1972)] or the flush ends ligation method using T4 ligase [Yuki Gosei Kagaku, 39, 110 (1972)], among others.

The vector DNA with the 5'-inosinate dehydrogenase gene region inserted therein in the above manner is used for transforming bacterial strains belonging to the genus Bacillus. The use of a 5'-inosinate dehydrogenase deficient, xanthine requiring mutant as such acceptor microorganism is advantageous in selecting the desired transformant. *Bacillus subtilis* RN-63 (IFO 14307, FERM-P 7410) is an example of the acceptor microorganism The recombinant DNA is introduced into such acceptor microorganism by the conventional transformation method such as the one described in Mol.Gen. Genet., 168, 111 (1973).

When the acceptor is a xanthine-requiring mutant, for instance, the desired transformant which carries the vector DNA with the 5'-inosinate dehydrogenase gene region inserted therein may be selected by isolating a strain capable of growing on a xanthine-free medium. When the vector DNA used contains a selection marker, such as resistance to certain antibiotic, addition of the antibiotic to the above-mentioned selective medium, for instance, can facilitate the selection of the desired transformant.

The thus-obtained recombinant vector DNA with the 5'-inosinate dehydrogenase gene region inserted therein can be extracted from the host strain for the subsequent introduction into another guanosine-producing microorganism or a 5'-inosinate dehydrogenase gene region-containing DNA fragment can be prepared from the recombinant DNA extracted and then inserted into another vector DNA for the subsequent introduction into a guanosine-producing microorganism. Alternatively, it is possible to clone the 5'-inosinate dehydrogenase gene region using a host-vector system in which the host-bacterium belongs to a genus other than the genus Bacillus, such as *Escherichia coli*, followed by preparation of a DNA fragment containing said gene region from the recombinant DNA thus obtained and insertion of said DNA fragment into a vector DNA suited for use in bacterial strains of the genus Bacillus, for introduction into a guanosine-producing microorganism.

The above-mentioned strain including *Bacillus subtilis* NA-6011, *Bacillus subtilis* NA-6012, *Bacillus subtilis* NA-7821 examples of such guanosine-producing microorganism.

Examples of the thus-obtained transformant include *Bacillus subtilis* TF11(IFO 14312, FERM P-7412), which is a transformant derived from the strain NA-6011, *Bacillus subtilis* TF21(IFO 14313, FERM P-7413), which is a transformant derived from the strain NA-6012, and the transformant NA-6128 (pBX 121'), which is a transformant derived from the strain NA-6128 (IFO 14373, FERM BP-617). The genetic characteristics of the plasmid introduced are expressed in these transformants, so that said transformants have higher chloramphenicol resistance, higher 5'-inosinate dehydrogenase activity and greater guanosine productivite as compared with the corresponding plasmids before transformation. However, other bacteriological properties are retained in the transformants.

The above-mentioned strains NA-6011, NA-6012 and NA-7821 are guanosine-producing strains derived from the parent strain *Bacillus subtilis* No. 115 and their bacteriological properties are as given in Table 1.

TABLE 1 a. Morphology

| | | |
|---|---|---|
| (1) | Shape and size | Rods, 0.8 × 3μ |
| (2) | Polymorphism | Single, rarely in pairs |
| (3) | Motility | Non-motile |
| (4) | Sporulation | Present |
| | Shape of spore | Ellipsoidal |
| | Swelling sporangium | No |
| | Position of spore | Central or para-central |
| (5) | Gram staining | Positive |
| (6) | Acid fastness | Negative | b. Cultural characteristics

| | | |
|---|---|---|
| (1) | Bouillon agar plate | Amorphous and diffused, rough surface, flat, opaque and white to light brown. |
| (2) | Bouillon agar slant | Flat, opaque and white to light brown. |
| (3) | Bouillon liquid | Coherent pallicle, no turbidity. |
| (4) | Litmus milk | Alkaline, peptonization, reduction. | c. Physiological characteristics

| | | |
|---|---|---|
| (1) | Reduction of nitrates | Positive |
| (2) | V-p test | Positive |
| (3) | Hydrolysis of starch | Positive |
| (4) | Utilization of citrate | Positive |
| (5) | Utilization of propionate | Negative |
| (6) | Utilization of ammonium salts | Positive |
| (7) | Urease | Weakly positive |
| (8) | Catalase | Positive |
| (9) | Oxygen requirement | Aerobic (no growth under anaerobic conditions) |
| (10) | Growth in 7% sodium chloride | Positive |
| (11) | Growth in media, pH 5.7 | Positive |
| (12) | Biotin requirement | Negative |

Consulting Bergy's Manual of Determinative Bacteriology, eighth edition, 1974, edited by R. E. Buchanan and N. E. Gibbons, the microorganisms having the above bacteriological characteristics were identified as strains belonging to the species *Bacillus subtilis*. The transformants TF11, TF12, NA-6128 (pBX 121') show the same bacteriological characteristics.

The IFO numbers used herein refer to accession numbers at the Institute for Fermentation, Osaka (IFO; 17-85 Jusohonmachi 2-chome, Yodogawa-ku, Osaka, Japan), the FERM P numbers to accession numbers at the Fermentation Research Institute, Agency of Industrial Science and Technology (FRI; 1–3 Yatabemachi Higashi 1-chome, Tsukubagun, Ibaraki Pref., Japan) and the FERM BP numbers to accession numbers at the FRI for deposits under the Budapest Treaty. Accession numbers and dates of deposit are listed as follows:

| Strain No. | FRI | IFO |
|---|---|---|
| *Bacillus subtilis* NA-6011 | FERM-BP 291 (Jul. 22, 1982) | IFO 14189 (Jul, 13, 1982) |
| *Bacillus subtilis* NA-6012 | FERM-BP 292 (Jul. 22, 1982) | IFO 14190 (Jul. 13, 1982) |
| *Escherichia coli* X-895 | FERM P-7411 (Jan. 25, 1984) | IFO 14308 (Dec. 27, 1983) |
| *Bacillus subtilis* RN-63 | FERM P-7410 (Jan. 25, 1984) | IFO 14307 (Dec. 27, 1983) |
| *Bacillus subtilis* TF 21 | FERM P-7413 (Jan. 25, 1984) | IFO 14313 (Jan. 13, 1984) |
| *Bacillus subtilis* TF 11 | FERM P-7412 (Jan. 25, 1984) | IFO 14312 (Jan. 13, 1984) |
| *Bacillus subtilis* NA-7821 | FERM BP-618 (Sept. 25, 1984) | IFO 14368 (Sept. 18, 1984) |
| *Bacillus subtilis* NA-6128 | FERM BP-617 (Sept. 25, 1984) | IFO 14373 (Sept. 18, 1984) |

Sub-cultures of the microorganisms, which were deposited on Jan. 25, 1982 at FRI under the accession numbers of FERM P as shown above, the deposit being converted to a deposit under the Budapest Treaty, have been stored at FRI under the accession numbers of FERM BP as follows:

| Strain | The Accession Numbers under the Budapest Treaty |
|---|---|
| *Escherichia coli* X-895 | FERM BP-614 |
| *Bacillus subtilis* RN-63 | FERM BP-613 |
| *Bacillus subtilis* TF-21 | FERM BP-616 |
| *Bacillus subtilis* TF 11 | FERM BP-615 |

The guanosine-producing transformants obtained in the above manner can be grown in the same manner as the cultivation of prior art guanosine producers (e.g. Japanese patent publications No. 46839/1976 and 33392/1973). Thus, as the medium, there is used a medium containing a carbon source, a nitrogen source, metal ions and further, if necessary, other nutrients such as amino acids, nucleic acids and vitamins. As the carbon source, there may be used glucose, sucrose, maltose, starch, saccharified starch, molasses, etc. As the nitrogen source, there may be used organic nitrogen sources such as peptone, corn steep liquor, soybean meal, yeast and urea as well as inorganic nitrogen sources such as ammonium salts (e.g. sulfate, nitrate, chloride carbonate), gaseous ammonia and aqueous ammonia, either alone or in combination. As other nutrients possibly required for the microbial growth, there may be used as necessary a variety of inorganic salts, amino acids, vitamins and so forth, either alone or in combination. As the adenine source, there may used not only adenine, adenosine, adenylic acid and nucleic acids but also microbial cells or extracts wherefrom containing these. To the medium, there may also be added an antiform or surfactant such as a silicone oil or polyethylene glycol ether, as necessary.

The cultivation is conducted generally under aerobic conditions, for example in the manner of shake culture or submerged culture under aeration and stirring. It is generally preferred that the pH of the medium is within the range of 4 to 9. In case a pH variation is observed in the medium, appropriate amounts of sulfuric acid, calcium carbonate, sodium hydroxide, gaseous ammonia, aqueous ammonia or the like may be added to the medium for adjusting the pH to a value falling within the preferred range. The incubation temperature is generally selected within the range of 20° C. to 45° C. such that it is fit for the microbial growth and guanosine accumulation. The incubation is continued until the guanosine accumulation substantially reaches a maximum. This end can be achieved generally by incubation for 24 hours to 144 hours.

For separation or recovery of guanosine from the culture, conventional methods of separation and purification, such as precipitation method and chromatography using an ion exchange resin or activated carbon, may be used (e.g. U.S. Pat. No. 3,912,587, Japanese patent publications Nos. 46839/1976 and 33392/1973).

The production method according to the invention can increase the guanosine productivity as compared with the case in which a strain before transformation is used.

The following examples are further illustrative of the present invention.

EXAMPLE 1

(i) Preparation of chromosomal DNA

The strain *Bacillus subtilis* NA-6012 (IFO 14190, FERM BP-292) capable of producing guanosine was inoculated into C medium (5 g/liter glucose, 0.5 g/liter sodium citrate, 5 g/liter Polypepton (Daigo Nutritive Chemicals. Ltd., Japan), 5 g/liter yeast extract, 1 g/liter $(NH_4)_2SO_4$, 7 g/liter $K_2HPO_4$, 3 g/liter $KH_2PO_4$, 0.2 g/liter $MgSO_4.7H_2O$, pH 7.0), followed by incubation at 37° C. overnight. From cells harvested from 1 liter of the culture, there was obtained a final amount of 8.0 mg of chromosomal DNA by the chromosomal DNA extraction method using phenol [Biochem. Biophys. Acta, 72, 619 (1963)].

(ii) Insertion of chromosomal DNA into pBR322

Unless otherwise specified, the conditions used in each restriction enzyme cleavage step mentioned hereinbelow were as described in the publication: T. Maniatis et al., Molecular Cloning, A Laboratory Manual, Cold Spring Harbor Laboratory, pages 98–103, 1982.

A 3-$\mu$g portion of the chromosomal DNA obtained in the above step i) was digested with the restrictron enzyme PstI (produced by Nippon Gene, Japan) at 37° C. for 60 minutes for DNA chain cleavage. After the enzyme was inactivated, ammonium acetate was added to a final concentration of 2.5 M, 2 volumes of cold alcohol was further added and, after cooling to −70° C., the precipitate DNA was collected by centrifugation. Sterilized water (35 $\mu$l) was added to said DNA precipitate for dissolution of the same. Separately, 1 $\mu$g of the EK system plasmid pBR322 was cleaved with the restriction enzyme PstI and the DNA was collected by centrifugation following the same procedure as above and dissolved in 35 $\mu$l of sterilized water. The thus-obtained chromosomal DNA fragment and pBR322 DNA fragment in solution were mixed and ligation was effected in 66 mM Tris-hydrochloric acid buffer (pH 7.5) containing 6.6 mM $MgCl_2$, 10 mM dithiothreitol and 660 $\mu$M ATP, using T4 phage-derived DNA ligase (Nippon Gene).

(iii) Transformation of xanthine-requiring strain of *Escherichia coli* with recombinant plasmid DNA A xanthine-requiring strain *Escherichia coli* X-895 (IFO 14308, FERM BP-614) gas obtained from the strain *Escherichia coli* C600 by the conventional method (replica plating method) of isolating auxotrophs.

Transformation of said strain with the recombinant plasmid was performed by the competent cell method [S. N. Cohen et al., Proc. Natl. Acad. Sci., U.S.A., 69, 2110 (1972)].

Thus, the strain Escherichia coli X-895 was grown on L medium (10 g/liter Bacto-Tryptone (Difco, U.S.A.), 5 g/liter yeast extract, 5 g/liter sodium chloride), cells were harvested and washed and competent cells were prepared by adding an ice-cooled calcium chloride solution. To this competent cell suspension, there was added the DNA solution prepared in the above step (ii) to thereby cause uptake of the plasmid DNA, namely transformation.

Then, M-9 CM agar plate (6 g/liter $Na_2HPO_4$, 3 g/liter $KH_2PO_4$, 0.5 g/liter sodium chloride, 1 g/liter ammonium chloride, 1 mM magnesium sulfate, 1 mM calcium chloride, 2 g/liter glucose, 2 g/liter casamino acids, 15 g/liter agar, pH 7.2) containing 15 $\mu$g/ml of tetracycline was spread with 3.1 ml of a suspension containing the above transformant, followed by incubation at 37° C. for 1 day. From the colonies formed on the agar plate medium, there was isolated a transformant *Escherichia coli* TEX-117 (tetracycline resistant but no longer xanthine-requiring).

(iv) Plasmid extraction from transformant

The recombinant plasmid was extracted from the transformant TEX-117 by the method described in the above-cited publication "Molecular Cloning", pages 86-93. Thus, *Escherichia coli* TEX-117 was inoculated into the above L medium, chloramphenicol was added for plasmid amplification, incubation was conducted overnight and cells were then harvested. The cells were washed, lysozyme was added and further 0.2 M sodium hydroxide containing 1% sodium lauryl sulfate was added for effecting bacteriolysis. Centrifugation following addition of 5 M potassium acetate gave a plasmid-containing supernatant. The plasmid DNA was precipitated by addition of 0.6 volume of isopropyl alcohol to the supernatant, washed with ethanol and dissolved in TE buffer (10 mM Tris-hydrochloric acid buffer, 1 mM EDTA, pH 8.0). Cesium chloride was added thereto to make the specific gravity 1.60 and then ethidium bromide was added to a final concentration of 600 $\mu$g/ml. Centrifugation was performed using a Beckman ultracentrifuge (roter $V_{65}$ Ti) at 20° C. and 50,000 rpm for 12 hours, a plasmid band detected under ultraviolet ray was collected, the ethidium bromide was removed by extraction with n-butanol, and dialysis was performed against TE buffer. The above procedure with 300 ml of the culture gave about 200 $\mu$g of the recombinant plasmid, which was named pEX117.

pEX117 was cleaved with various restriction enzymes as shown in FIG. 1 and the digests were subjected to agarose gel electrophoresis with a Hind III digest of $\lambda$-phase (produced by Nippon Gene) as the molecular weight standard. The electrophoretic patterns gave the restriction enzyme cleavage map shown in FIG. 1. pEX117 is a recombinant plasmid with an about 6.4 kilo base DNA fragment inserted in pBR322 at the PstI site thereof.

EXAMPLE 2

(i) 3 μg of pEX117 was partially digested with the restriction enzyme Hind III. Separately, pBR322 was completely digested with Hind III. Both the digests were mixed and ligated together by the method described under ii) in Example 1 using T4 phage-derived DNA ligase. This DNA solution was used for transformation of *Escherichia coli* X-895 by the procedure described under iii) in Example 1. Tetracycline resistant strains were thus obtained and a transformant which was no longer xanthine-requiring, i.e. *Escherichia coli* TEX-147, was obtained from among them. About 220 μg of recombinant plasmid was obtained from said transformant by plasmid extraction conducted by the method shown in Example 1-iv). The plasmid was named pEX147. The restriction enzyme cleavage map of pEX147 is shown in FIG. 2. pEX147 is a recombinant plasmid derived from pBR322 by insertion of a 2.9 kilo base DNA fragment at the Hind III site thereof.

(ii) About 200 μg of the recombinant plasmid pEX147 was partially digested with the restriction enzyme Hind III and the digest was subjected to gel electrophoresis using low melting point agarose (Bethesda Research Laboratories Incorporation, U.S.A.). A portion of the agarose gel corresponding to the travel distance of a 2.9 kilo base DNA was cut off and DNA was extracted from said agarose gel section by the method described in the above-cited publication "Molecular Cloning", page 170. Finally, about 2 μg of DNA was obtained. Restriction enzyme cleavage patterns confirmed that said DNA was the 2.9 kilo base DNA inserted in pBR322 at Hind III site thereof.

EXAMPLE 3

(i) Insertion of 5'- inosinate dehydrogenase gene into BS-system vector (pC194)

3 μg of pEX117 was partially digested with the restriction enzyme Hind III and, separately, the plasmid pC194, the host of which was *Bacillus subtilis*, was completely digested with Hind III. Both the digests were mixed and ligated together by the method described in Example 1-ii) using T4 phage-derived DNA ligase.

(ii) Transformation of xanthine-requiring strain of *Bacillus subtilis* with recombinant plasmid DNA A xanthine-requiring strain of *Bacillus subtilis*, i.e. the strain RN-63 (IFO 14307, FERM BP-613) was obtained from the strain *Bacillus subtilis* MI-114 (genetical characteristics: trpC2, leu8, r−, m−) by the conventional method of isolating auxotrophs.

Then, *Bacillus subtilis* RN-63 was transformed with the DNA solution prepared in the above step i) to give chloramphenicol resistant transformants. The transformation was effected by the method comprising causing DNA uptake under the action of polyethylene glycol on the protoplast of said auxotroph [S. Chang and S. N. Cohen, Mol. Gen. Genet., 168, 111 (1979)].

As a result of the above transformation procedure, a transformant *Bacillus subtilis* TX-121 was obtained as follows: transformants growth on a regeneration medium containing 10 μg/ml of chloramphenicol were replica-plated onto an agar plate of M-9 CMTL medium (M-9 medium supplemented with 50 μg/ml each of tryptophan and leucine) containing 10 μg/ml of chloramphenicol. After incubation at 37° C. for 1 day, the strain *Bacillus subtilis* TX-121 was obtained which is resistant to chloramphenicol and at the same time requires no xanthine for growth.

(iii) Plasmid extraction from transformant

The strain *Bacillus subtilis* TX-121 was grown on 300 ml of the above-mentioned L medium and about 100 μg of plasmid was obtained from the resulting culture by the method described above under (iv) in Example 1. This plasmid was named pBX121. The restriction enzyme cleavage map of the recombinant plasmid pBX121 is as shown in FIG. 3, the size of the insert fragment being about 2.9 kilo bases.

EXAMPLE 4

Production of guanosine using *Bacillus subtilis* transformant

*Bacillus subtilis* NA-6012 (IFO 14190, FERM BP-292) was transformed with pBX121 in accordance with the method described in Example 3 under ii). A regeneration medium containing 10 μg/ml chloramphenicol was spread with a suspension containing the transformant, followed by incubation at 37° C. for 5 days, and a chloramphenicol resistant transformant *Bacillus subtilis* TF21 (IFO 14313, FERM BP-616) was obtained from the colonies formed.

Then, 20 ml of a seed medium specified in Table 2 as placed in a 200-ml Erlenmeyer flask was inoculated with one loopful of *Bacillus subtilis* TF21. After shaking at 37° C. for 18 hours, 1 ml of the medium was inoculated into 20 ml of a fermentation medium specified in Table 2 and placed in a 200-ml creased flask, followed by incubation on a rotary shaker at 37° C. for 4 days. A guanosine accumulation of 18.0 mg/ml was attained in the fermentation broth.

The same cultivation procedure as above using about 50 flasks gave 1 liter of culture of substantially the same quality. The culture was adjusted to pH 11 with sodium hydroxide to thereby dissolve guanosine crystals, bacterial cells were then removed by centrifugation, and the supernatant obtained was neutralized and cooled to cause precipitation of guanosine. The crude crystals thus obtained were dissolved in 700 ml of hot water, the solution was decolorized with activated carbon and guanosine precipitation was allowed to proceed in the cold. Thus was obtained 14.5 g of purified crystals of guanosine. The purity of said purified crystals was 93%. For comparison, the recombinant plasmid pBX121-free strain, i.e. *Bacillus subtilis* NA-6012, was cultivated under the same conditions as above, and the guanosine accumulation was found to be 14 mg/ml.

TABLE 2

| Seed culture medium | | Fermentation medium | |
|---|---|---|---|
| Component | Concentration | Component | Concentration |
| Sorbitol | 2.0% | Glucose | 15.0% |
| Dry yeast | 1.5% | Ammonium sulfate | 2.0% |
| Monopotassium phosphate | 0.1% | Urea | 1.0% |
| | | Sodium glutamate | 1.0% |
| Dipotassium phosphate | 0.3% | Corn steep liquor | 2.0% |
| Histidine | 0.01% | Nucleic acids (purity 80%) | 0.2% |
| | | Calcium chloride | 0.5% |
| | | Magnesium sulfate | 0.2% |

TABLE 2-continued

| Seed culture medium | | Fermentation medium | |
|---|---|---|---|
| Component | Concentration | Component | Concentration |
| | | Potassium chloride | 0.05% |
| | | Calcium carbonate | 3.0% |
| | | Biotin | 200 µg/liter |
| | | Manganese sulfate | 2.5 mg/liter |

EXAMPLE 5

*Bacillus subtilis* NA-6011 (IFO 14189, FERM BP-291) was transformed with pBX121 following the procedure described in Example 3-ii) and a chloramphenicol resistant transformant *Bacillus subtilis* TF11 (IFO 14312, FERM BP-615) was isolated and cultivated under the same conditions as used in Example 4. The guanosine accumulation amounted to 16.0 mg/ml. The subsequent guanosine purification by the procedure described in Example 4 gave, from 1 liter of fermentation broth, 13.1 g of 91% pure crystalline guanosine. Cultivation of the recombinant plasmid pBX121-free strain, i.e. *Bacillus subtilis* NA-6011, under the same conditions as above resulted in accumulation of 5.0 mg/ml of guanosine.

EXAMPLE 6

5'-Inosinate dehydrogenase activity of transformant

MEA medium (10 g/liter Polypepton, 5 g/liter yeast extract, 5 g/liter sodium chloride, 5 g/liter sodium glutamate, 0.5 g/liter magnesium sulfate, 0.1 g/liter calcium chloride, 50 g/liter glucose, pH 7.2) was inoculated with the strain *Bacillus subtilis* TX-121, followed by incubation at 37° C. overnight. Cells were harvested, washed, suspended in 1/10 volume of 0.05 M phosphate buffer (pH 7.2) containing 5 mM glutathione (reduced form) and sonicated. The residue was removed by centrifugation and the supernatant was dialyzed against the above phosphate buffer overnight to give a crude enzyme solution. Said crude enzyme solution was assayed for 5'-inosinate dehydrogenase activity by the method of B. Magasanik (Methods in Enzymology, VI, pages 106–110, Academic Press, New York, 1963). The enzyme activity thus found was 0.02 unit/mg protein. The recombinant plasmid-free host, i.e. *Bacillus subtilis* RN-63 was assayed for 5'-inosinate dehydrogenase activity in the same manner and found to be quite lacking in the enzyme activity.

EXAMPLE 7

In accordance with the method described in Example 1, the chromosomal DNA of *Bacillus subtilis* NA-7821 (IFO 14368, FERM BP-618) capable of producing guanosine was digested with the restriction enzyme Pst I and the obtained DNA fragment was ligated with the cleaved pBR322, and thus plasmid pEX117' which complements xanthine-requiring of *Escherichia coli* X-895 was obtained. pEX117' was partially digested with the restriction enzyme Hind III and ligated with plasmid pC194, by the method described in Example 3, to give plasmid pBX121' having a 5'-inosinate dehydrogenase gene and further having a Hind III cleavage site 2.9 kilo base pairs.

Then, *Bacillus subtilis* NA-6128 (IFO 14373, FERM BP-617) was transformed with plasmid pBX121' in accordance with the method described in Example 4. The thus obtained transformant NA-6128 (pBX121') was inoculated into a fermentation medium containing 10% glucose, 2% ammonium sulfate, 1% urea, 1% sodium glutamate, 2% corn steep liquor, 0.2% RNA, 0.5% calcium chloride, 0.2% magnesium sulfate, 0.05% potassium chloride, 2.5 mg manganese sulfate and 3% calcium carbonate, followed by incubation on a rotary shaker at 37° C. for 3 days. A guanosine accumulation of 20 mg/ml was attained in the fermentation broth. For comparison, the recombinant plasmid pBX121'-free strain, i.e. *Bacillus subtilis* NA-6128, was cultivated under the same conditions as above, and the guanosine accumulation was found to be 7 mg/ml.

In the above, the strain NA-7821 and the strain NA-6128 were introduced from the strain NA-6012 and the strain NA-6011 by N-methyl-N'-nitro-N-nitrosoguanidine (NTG) treatment, respectively.

BRIEF DESCRIPTION OF THE DRAWINGS

FIGS. 1, 2 and 3 are the restriction enzyme cleavage maps of the recombinant Plasmids pEX117, pEX147 and pBX 121, which were obtained in the examples, respectively. In the figures, the numerical values in the parentheses each indicates the number of base pairs (in kilo base pairs).

Figure 1:
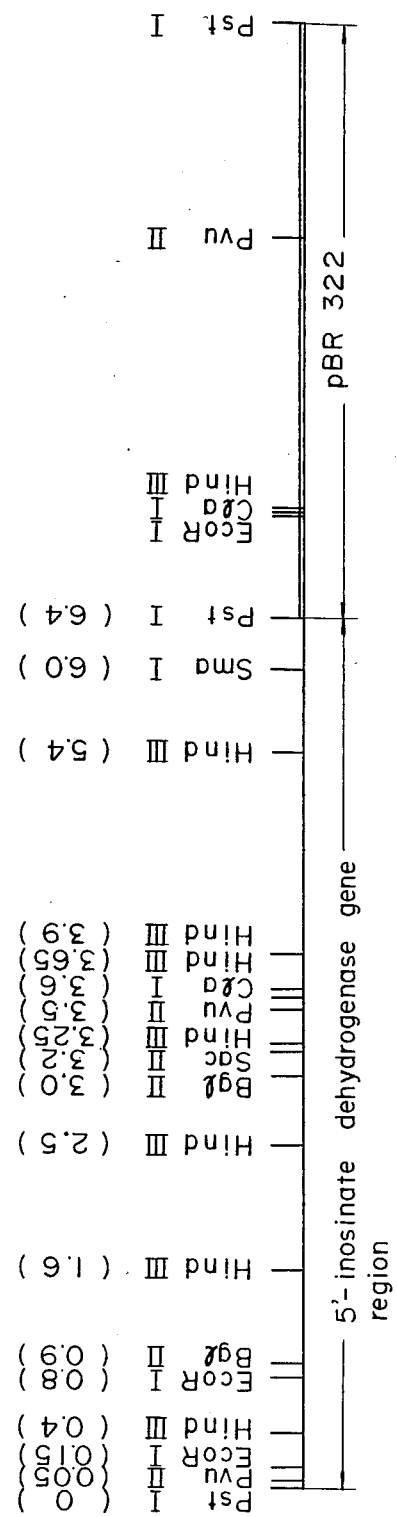

What we claim is :

1. A recombinant DNA having a 5'-inosinate dehydrogenase gene and further having a Hind III cleavage site 2.0 kilo base pairs apart therefrom, said DNA obtained from the chromosomal DNA of a Bacillus strain capable of producing guanosine, xanthosine or both guanosine and xanthosine.

2. The DNA according to claim 1, wherein the *Bacillus* strain is *Bacillus subtilis* NA-6011 (IFO 14189, FERM BP-291), *Bacillus subtilis* NA-6012 (IFO 14190, FERM BP-292), *Bacillus subtilis* NA-7821 (IFO 14368, FERM BP-618), *Bacillus subtilis* ATCC 19221, *Bacillus pumilus* NA-1102 (IFO 14185, FERM BP-289) or *Bacillus pumilus* NA-1103 (IFO 14186, FERM BP-290).

3. A vector with the DNA of claim 1 inserted therein.

4. A Bacillus strain transformed with the vector of claim 3.

5. The Bacillus strain according to claim 4, wherein said strain is capable of producing guanosine.

6. A method of producing quanosine which comprises cultivating in a medium a guanosine-producing Bacillus strain transformed with a vector containing a 5'-inosinate dehydrogenase gene region obtained from the chromosomal DNA of a Bacillus strain capable of producing guanosine, Xanthosine or both guanosine and xanthosine and harvesting the guanosine so produced in the culture medium.

* * * * *

UNITED STATES PATENT AND TRADEMARK OFFICE
CERTIFICATE OF CORRECTION

PATENT NO. : 4,749,650
DATED : June 7, 1988
INVENTOR(S) : Kenichiro, etal.

It is certified that error appears in the above—identified patent and that said Letters Patent is hereby corrected as shown below:

At column 10, line 37, "2.0" is changed to --2.9--.

At column 10, line 58, "Xanthosine" is changed to --xanthosine--.

Signed and Sealed this

Third Day of January, 1989

Attest:

DONALD J. QUIGG

Attesting Officer  Commissioner of Patents and Trademarks